United States Patent
Braxton, Jr.

(10) Patent No.: US 12,390,232 B2
(45) Date of Patent: Aug. 19, 2025

(54) POWERED OSTEOTOME TREPANATION TOOL

(71) Applicant: INTEGRITY IMPLANTS INC., Palm Beach Gardens, FL (US)

(72) Inventor: Ernest Earl Braxton, Jr., Vail, CO (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 234 days.

(21) Appl. No.: 18/021,781

(22) PCT Filed: Aug. 18, 2021

(86) PCT No.: PCT/US2021/046492
§ 371 (c)(1),
(2) Date: Feb. 17, 2023

(87) PCT Pub. No.: WO2022/040305
PCT Pub. Date: Feb. 24, 2022

(65) Prior Publication Data
US 2023/0346393 A1 Nov. 2, 2023

Related U.S. Application Data

(60) Provisional application No. 63/103,670, filed on Aug. 18, 2020.

(51) Int. Cl.
*A61B 17/17* (2006.01)
*A61B 17/16* (2006.01)

(52) U.S. Cl.
CPC .......... *A61B 17/1757* (2013.01); *A61B 17/16* (2013.01); *A61B 17/17* (2013.01); *A61B 2017/1602* (2013.01)

(58) Field of Classification Search
CPC .................................................. A61B 17/1757
See application file for complete search history.

(56) References Cited

U.S. PATENT DOCUMENTS 5,722,977 A 3/1998 Wilhelmy
6,007,496 A 12/1999 Brannon
(Continued)

FOREIGN PATENT DOCUMENTS

CN 210009092 U 2/2020

OTHER PUBLICATIONS

PCT Notification of Transmittal of the International Search Report and the Written Opinion of the International Searching Authority, or the Declaration issued to counterpart Application No. PCT/US2021/046492 dated Dec. 9, 2021.

*Primary Examiner* — Christian A Sevilla
(74) *Attorney, Agent, or Firm* — McNees Wallace & Nurick LLC

(57) ABSTRACT

A surgical bone cutting system includes a trajectory guide and an osteotome or trepanation tool with a generally square cutting tip that creates a corridor through bone, for example, in the context of spine, through a facet joint or other vertebral structure and to the disc space between two vertebrata for any of a variety of surgical procedures, including but not limited to disc prep and cage insertion. The osteotome fits into the trajectory guide to contact bone and effect creating a bony corridor. In some embodiments, the trajectory guide includes a cylindrical allograft collection chamber, and the trajectory guide and osteotome fit into standard tubular retractors and are agnostic with respect to receiving standard drill bits or a powered auger insertable through a center through channel.

20 Claims, 5 Drawing Sheets

(56) References Cited

U.S. PATENT DOCUMENTS

| | | |
|---|---|---|
| 7,670,328 B2 * | 3/2010 | Miller ............... A61B 17/1622 |
| | | 606/167 |
| 7,803,159 B2 | 9/2010 | Perez-Cruet et al. |
| 8,118,813 B2 | 2/2012 | Perez-Cruet et al. |
| 8,571,638 B2 | 10/2013 | Shoham |
| 8,915,921 B2 | 12/2014 | Ralph et al. |
| 9,642,633 B2 | 5/2017 | Frey et al. |
| 9,826,986 B2 | 11/2017 | Donner et al. |
| 10,806,470 B2 | 10/2020 | Lipari et al. |
| 2004/0002711 A1 * | 1/2004 | Berry ............... A61B 17/1757 |
| | | 606/79 |
| 2004/0191897 A1 * | 9/2004 | Muschler ......... A61B 17/32002 |
| | | 435/325 |
| 2004/0193170 A1 * | 9/2004 | Kemppainen ......... A61F 2/4601 |
| | | 606/92 |
| 2007/0118136 A1 | 5/2007 | Ek |
| 2007/0191852 A1 | 8/2007 | Shimko et al. |
| 2008/0081951 A1 | 4/2008 | Frasier et al. |
| 2008/0125856 A1 * | 5/2008 | Perez-Cruet ....... A61B 17/1671 |
| | | 623/1.23 |
| 2009/0118742 A1 | 5/2009 | Hartmann et al. |

\* cited by examiner

POWERED OSTEOTOME TREPANATION TOOL

RELATED APPLICATION

The present application claims priority to U.S. Provisional Application No. 63/103,670 titled POWERED OSTEOTOME TREPANATION, which was filed on Aug. 18, 2020, the entirety of which is incorporated herein by reference.

FIELD OF THE INVENTION

The present disclosure is generally directed to instruments and related methods for bone and/or tissue removal. More particularly, the present disclosure is directed to handheld resected bone and/or tissue removal instruments and related methods for establishing a marked site on a bone and for removing a resected bone portion from a patient.

BACKGROUND OF THE INVENTION

A bone or tissue may be resected (i.e., the excision of a portion of the bone) in any number of ways for any number of reasons. For example, adjacent portions of two or more bones or tissue forming a joint therebetween may be resected, and the bones may be reduced to promote fusion of the bones. As another example, during an arthrodesis procedure in the spine to obtain access to the disc base. In a transforaminal lumbar interbody fusion procedure, for example, the superior and inferior articular facets are removed promote fusion between the disc space of the rostral and caudal spinal segment.

A bone may be resected using a device that cuts through the bone to separate a portion therefrom, and subsequent removal of the portion from the patient. This tissue is relatively difficult to remove from the resected bone portion, and thus makes removal of the resected bone portion difficult. A Kerrison rongeur, curette, burr, bone scalpel blade, osteotome, or other device is typically used to resect such tissue. The resected bone portion may thereby include some of such tissue connected thereto after resection.

Typical methods of removing a resected bone portion include the manual use of a tool, such as a rongeur, curette, osteotome and/or hemostat, to physically engage the portion and extract the portion from the patient. However, removal of a resected bone portion may be relatively difficult. For example, the resected bone portion may be positioned in a relatively tight, flat joint space which restricts access to the resected bone portion. As another example, the resected bone portion may be attached to at least one tendon, ligament or other soft tissue that is relatively difficult to resect or otherwise makes removal of the resected bone portion challenging.

Therefore, bone and/or tissue removal instruments and related methods that fit into tight spaces or joints, adequately remove soft tissue from resected bone or tissue portions, and securely engage resected bone are desirable.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

REFERENCE NUMBERS USED IN THE SPECIFICATION AND DRAWINGS

Figure 1:
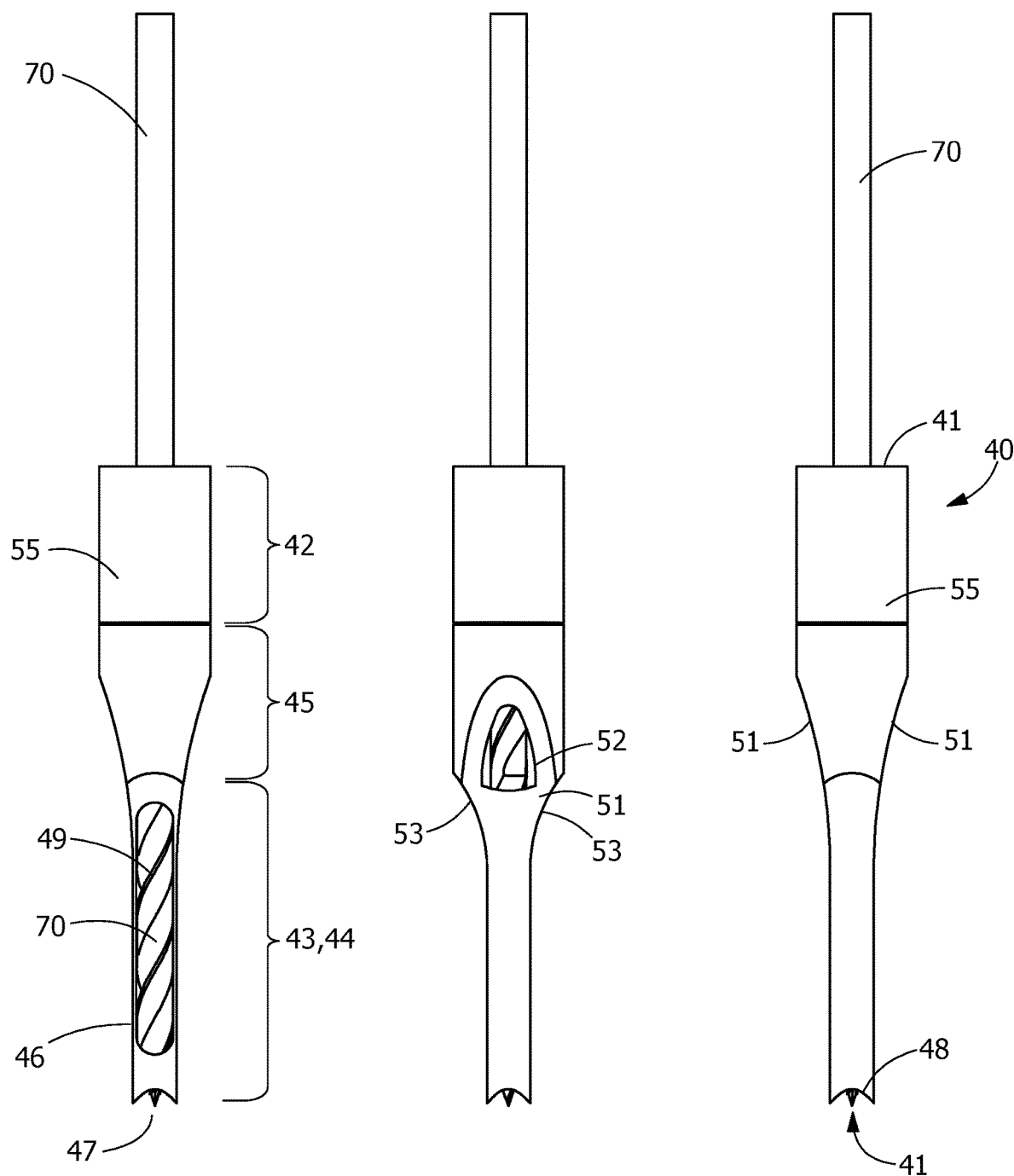
FIG. 1 shows first, second and third side views of a first embodiment of an osteotome of the surgical bone cutting system.
Figure 2:
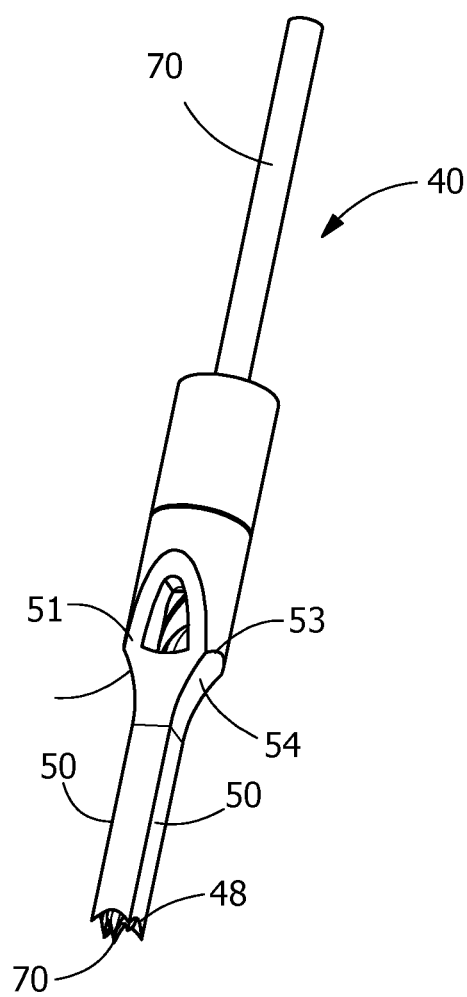
FIG. 2 shows a perspective view from the second side view of the first embodiment of an osteotome of the surgical bone cutting system shown in FIG. 1.
Figure 3:
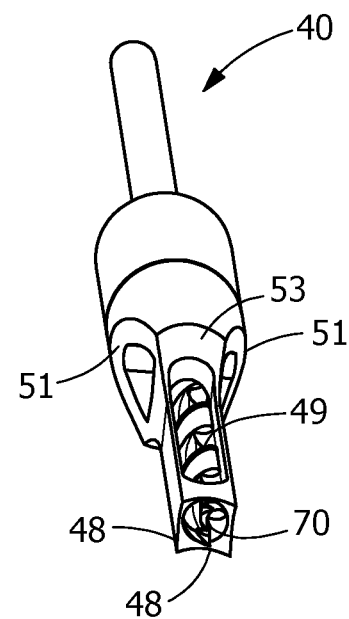
FIG. 3 shows a bottom perspective view from the first side view of the first embodiment of an osteotome of the surgical bone cutting system shown in FIG. 1.

The following table provides a key to the specific features mentioned in the specification which are numbered in the text or otherwise correspond to the indicated numbers in the table.

| Referenced Feature | Ref # |
| --- | --- |
| surgical bone cutting system | 100 |
| trajectory guide | 10 |
| Hollow chamber | 11 |
| proximal and distal openings | 12, 13 |
| inner wall of the trajectory guide | 15 |
| osteotome | 40 |
| through channel | 41 |
| proximal portion | 42 |
| distal portion | 43 |
| cutting jig | 44 |
| central portion | 45 |
| guide shaft | 46 |
| distal cutting tip | 47 |
| concave radiused cutting edges | 48 |
| elongate slot aperture | 49 |
| opposing walls of the guide shaft | 50 |
| first pair of opposing sides | 51 |
| elongate aperture that tapers towards the guide shaft | 52 |
| Second pair of opposing sides | 53 |
| concave radiused taper | 54 |
| outer wall of the osteotome | 55 |
| drill bit | 70 |
| generally cylindrical surgical retractor | 80 |
| proximal handle | 81 |
| distal retractor end | 82 |
| a support substrate | 95 |
| Surgical subject | 96 |
| locking arm | 99 |
| robotic arm | 99 |
| target trajectory | 90 |
| robot | R |
| alignment/navigation system | S |

Features and advantages of the general inventive concepts will become apparent from the following description made with reference to the accompanying drawings, including drawings represented herein in the attached set of figures, of which the following is a brief description.

SUMMARY OF THE INVENTION

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

In some embodiments, the instant disclosure provides a first embodiment of a surgical bone cutting system that includes a trajectory guide that includes opposing proximal and distal openings and has a generally cylindrical shape, and an osteotome having a through channel suitable for receiving a drill bit or auger inserted therethrough, wherein the osteotome also includes a proximal portion, a distal portion that includes a cutting jig, and a central portion between the proximal portion and the distal portion, the cutting jig including a guide shaft and a distal cutting tip, the guide shaft being tapered relative to at least the proximal portion, and the distal cutting tip having a square or rectangular cross-sectional shape and including opposing pairs of concave radiused cutting edges suitable for penetrating bone. In some embodiments, the trajectory guide and osteotome are configured to be arranged by passage of at least a portion of the distal portion of the osteotome through the proximal opening of the trajectory guide. In some embodiments, the surgical bone cutting system also includes a bone drill or auger comprising a bit suitable for penetrating bone. The bone drill or auger may be manually or electrically powered. In some examples, the bone drill may be ultrasonic or harmonic.

In some embodiments, the trajectory guide defines a generally hollow bone collection chamber between its proximal and distal openings, and the trajectory guide is sized and shaped for insertion within a generally cylindrical surgical retractor that comprises a proximal handle and a distal retractor end for contacting bone.

In some embodiments, the instant disclosure provides a second embodiment of a surgical bone cutting system that includes a trajectory guide including opposing proximal and distal openings and an osteotome having a through channel, and including a proximal portion, a distal portion including a cutting jig, and a central portion between the proximal portion and the distal portion, the cutting jig including a guide shaft and a distal cutting tip, the guide shaft being tapered relative to at least the proximal portion, and the distal cutting tip having a square or rectangular cross-sectional shape and including opposing pairs of concave radiused cutting edges suitable for penetrating bone. In some embodiments, the trajectory guide and osteotome are configured to be arranged by passage at least the distal portion of the osteotome through the proximal opening of the trajectory guide, the osteotome have a maximum outer diameter that is less than an inner diameter of the trajectory guide to effectively control the trajectory of the inserted osteotome along a trajectory established by the trajectory guide when it is secured to the locking arm and the locking arm is fixed relative to the support substrate In some embodiments, the surgical bone cutting system also includes a bone drill or auger comprising a bit suitable for penetrating bone, a support substrate, and a locking arm, the support substrate configured to retain a surgical subject in a secured and fixed position, the locking arm configured to retain the trajectory guide in a secured and fixed position relative to the support substrate, the surgical subject, or both, In some embodiments, the locking arm is a robotic arm, and the surgical bone cutting system further includes an alignment and navigational system and a robot that is controlled by the navigational system to align the trajectory guide when connected to a robotic arm of the robot within a three dimensional space based on predetermined coordinates, wherein the three dimensional space is defined by coordinates and includes at least a portion of the support substrate, at least a portion of the surgical subject, or both.

In some embodiments, the instant disclosure provides a first method for excising bone from a clinical subject. In some embodiments, the method includes the step of providing a surgical bone cutting system that includes a trajectory guide including opposing proximal and distal openings and having a generally cylindrical shape, and an osteotome having a through channel suitable for receiving a bit suitable for penetrating bone inserted therethrough, and including a proximal portion, a distal portion including a cutting jig, and a central portion between the proximal portion and the distal portion, the cutting jig including a guide shaft and a distal cutting tip, the guide shaft being tapered relative to at least the proximal portion, and the distal cutting tip having a square or rectangular cross-sectional shape and including opposing pairs of concave radiused cutting edges suitable for penetrating bone. In some embodiments, the method includes providing a bone drill or auger and a bit suitable for penetrating bone suitable for drilling bone.

In some embodiments, the method also includes the steps of establishing access to a surgical site adjacent a bone of a surgical subject; positioning and fixing the trajectory guide in a selected position with respect to the surgical site; and directing at least a portion of the distal portion of the osteotome through the proximal opening of the trajectory guide and securing the osteotome into engagement with bone in the surgical site.

In some embodiments, the step of establishing access to the surgical site includes securing a cylindrical retractor to the surgical subject, wherein the trajectory guide is sized and shaped for insertion within the cylindrical surgical retractor and defines a generally hollow bone collection chamber between its proximal and distal openings.

In some embodiments, the method for excising bone further includes the steps of mechanically driving at least a portion of the distal cutting tip into bone followed by passing the bone drill or auger within the through channel of the osteotome and into contact with bone and activating the drill or auger to remove bone tissue.

In some embodiments, the instant disclosure provides a second method for excising bone from a clinical subject using a predetermined trajectory for access to the surgical site, for example, employing coordinates for a target trajectory relative to the surgical site within a three dimensional space, wherein the three dimensional space is defined by coordinates that include at least a portion of the support substrate, at least a portion of the surgical subject, or both, the method including affixing the trajectory guide to a locking or robotic arm, and directing motion of the robotic arm to position the trajectory guide into alignment with the target trajectory.

In some embodiments, the osteotome has a maximum outer diameter that is less than an inner diameter of the trajectory guide. In some embodiments, the surgical bone cutting system further includes a support substrate; and a locking arm, the support substrate configured to retain the surgical subject in a secured and fixed position, the locking arm configured to retain the trajectory guide in a secured and fixed position relative to the support substrate, the surgical subject, or both.

In some embodiments, the method for excising bone further includes, after the step of establishing access to the surgical site, securing the trajectory guide to the locking arm and fixing the locking arm relative to the support substrate; and passing at least the distal portion of the osteotome through the proximal opening of the trajectory guide whereby interference between an outer wall of the osteotome and an inner wall of the trajectory guide effectively controls the trajectory of the inserted osteotome along a trajectory established by the trajectory guide.

In some embodiments, the locking arm is a robotic arm, the surgical bone cutting system further including an alignment and navigational system that comprises a robot that is controlled by the navigational system.

In some embodiments, the method for excising bone further includes providing coordinates for a target trajectory relative to the surgical site within a three dimensional space, wherein the three dimensional space is defined by coordinates and includes at least a portion of the support substrate, at least a portion of the surgical subject, or both, and the method further includes the steps of affixing the trajectory guide to the robotic arm, and directing motion of the robotic arm to position the trajectory guide into alignment with the target trajectory.

In various embodiments, the step of establishing access to the surgical site may include selecting a surgical site within a human spine wherein the selected surgical site is adjacent bone, for example, a facet joint, and the method for excising bone further includes a step selected from the group consisting of (1) mechanically driving at least a portion of the distal cutting tip into bone followed by removing the osteotome from the trajectory guide, (2) mechanically driving at least a portion of the distal cutting tip into bone followed by passing the bone drill or auger within the through channel of the osteotome and into contact with bone and activating the drill or auger to remove bone tissue, and (3) a combination thereof.

In another aspect, the present disclosure provides a powered osteotome device which, when combined with a system for navigation or stabilization guide, facilitates bone resection. In some embodiments, the instrument includes a first elongate member, a second elongate member. The first elongate member includes a cutting chisel edge defining the corridor for bone removal. The second elongate member is rotatably coupled to the first elongate to safely remove bone along the guide jig provided by the first member. The second head portion includes an interior surface with a front cutting tooth defining a free end of the second head portion, a substantially flat bone or irregular engagement surface, and gripping teeth extending between the front cutting tooth and the bone engagement surface.

In another aspect, the present disclosure provides for a method of removing a resected bone portion. The powered osteotome method includes integration with computer-assisted surgery and robotics. Combination with ultrasonic aspirator and use with electronic or pneumatic drilling devices.

In another aspect, the present disclosure provides a surgical instrument. The surgical instrument includes a first elongate member including guide jig and stabilization arm for trephination to the planned surgical target. The target may represent the disc space in the spine. The second rotating member fits within the first mother member to facilitate bone removal and collection.

In some embodiments, the invention can provide a bony corridor to the disc space front cutting tooth a distance within the range of 5 mm to 20 mm. In some such embodiments, the instrument further includes a biasing mechanism that biases the first and second member away from vital structures such as but not limited to nerve roots. Handle portions or stabilization guide attached to the operating table.

In some embodiments, the movable second member rotation point is formed via a stabilization guide and/or wire extending into the bone or facet joint.

In another aspect, the present disclosure provides for a method of removing and collecting resected bone or tissue portion from a body.

In some embodiments, the first head portion includes a substantially smooth interior tissue engagement surface to engage the bone without skiving or migration In some embodiments, the resected bone may be used as morselized allograft for the arthrodesis procedure.

These and other objects, features and advantages of this disclosure will become apparent from the following detailed description of the various aspects of the disclosure taken in conjunction with the accompanying drawings.

DETAILED DESCRIPTION

This description describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

As used herein, the singular forms "a," "an," and "the" are intended to include the plural forms as well, unless the context clearly indicates otherwise.

Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care. A "clinical subject" refers to a human or other animal who is the subject of treatment with a bone fixation or reduction device in accordance with the disclosure. With respect to any references herein that may be made relative to a clinical subject, the term "medial" indicates a direction toward the centerline axis (e.g., the spine) of the clinical subject, and the term "lateral" indicates a direction toward a side of the clinical subject. The term "system" refers to any combination of two or more of objects, devices, or components. And the term "method" refers to any one of methods of using a device or system, and surgical methods or techniques employing a device or system.

Referring now to the drawings as variously depicted in FIG. 1-FIG. 7, the present invention includes a surgical bone cutting system 100 that is useful for penetrating and/or removing bone tissue from a clinical subject. In some embodiments, the bone cutting system 100 and methods are useful for spinal applications, for example, surgeries performed on the facet joints of the spine. Surgeries on the facet joints are often performed to reduce pain by reliving pressure and in some instances improving the stability of the motion segment. In such instances, fusion of adjacent vertebrae may be performed when a significant portion of a facet is removed. Other examples of surgery that may be performed using the disclosure system, in either open or using a minimally invasive approach and/or endoscopically, include decompression, reduction, or facetectomy. Though this disclosure includes description of embodiments of the invention used for facet joint surgery, it will be appreciated that the use of the system is not limiting, and it may be employed for other applications through the anatomy of clinical subject.

Figure 4:
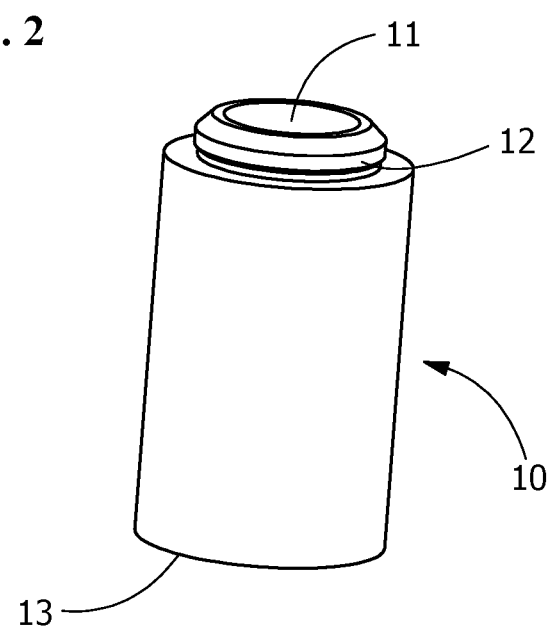
FIG. 4 shows a first embodiment of a trajectory guide of an osteotome of the surgical bone cutting system.

Referring now to FIGS. 1-5, the drawings, respectively, show: first, second and third side views of a first embodiment of an osteotome of the surgical bone cutting system, a perspective view from the second side view of the first embodiment of an osteotome of the surgical bone cutting system shown in FIG. 1; a bottom perspective view from the first side view of the first embodiment of an osteotome of the surgical bone cutting system shown in FIG. 1; a first embodiment of a trajectory guide of an osteotome of the surgical bone cutting system; and a first embodiment of surgical bone cutting system including the first embodiment of an osteotome as shown in FIG. 1 and the first embodiment of a trajectory guide as shown in FIG. 4 and a prior art cylindrical surgical retractor, all depicted in an exploded view relative to an assembly thereof.

Figure 5:
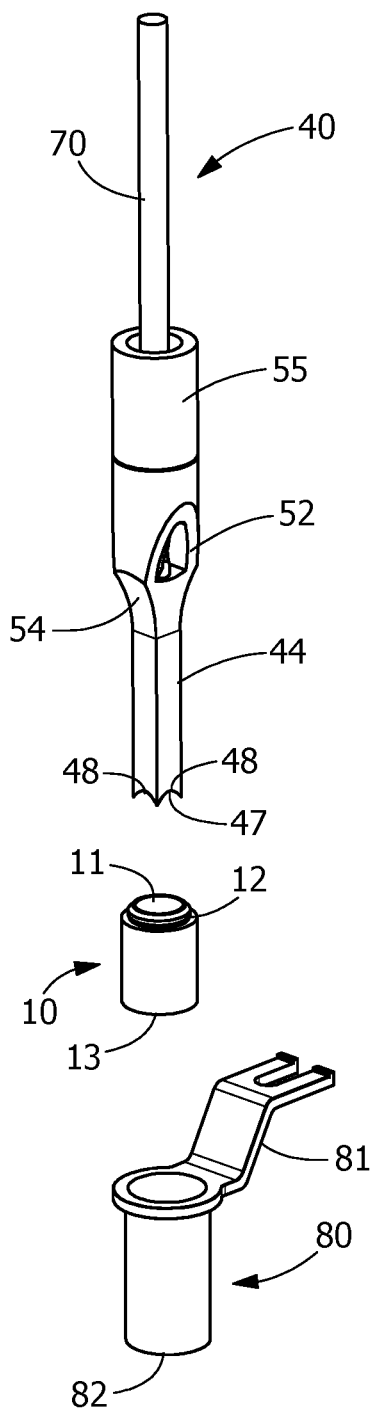
FIG. 5 shows a first embodiment of surgical bone cutting system including the first embodiment of an osteotome as shown in FIG. 1 and the first embodiment of a trajectory guide as shown in FIG. 4 and a prior art cylindrical surgical retractor, all depicted in an exploded view relative to an assembly thereof.

Referring now to FIG. 5, the invention provides a surgical bone cutting system 100 that includes a trajectory guide 10 and an osteotome 40 or trepanation tool with a generally square cutting tip 47 that creates a corridor through bone, for example, in the context of spine, through a facet joint or other vertebral structure and to the disc space between two vertebrata for any of a variety of surgical procedures, including but not limited to disc prep and cage insertion. It will be appreciated that in various embodiments, the cutting tip 47 may be square in cross-section as depicted in the embodiments of the drawings herein, while in other embodiments it may have another polyhedral type of cross-sectional shape that is other than square in cross section, or it may be generally circular or elliptical in cross section. Further, in various embodiments, the guide shaft 46 may be square in cross-section as depicted in the embodiments of the drawings herein, while in other embodiments it may have another polyhedral type of cross-sectional shape that is other than square in cross section, or it may be generally circular or elliptical in cross section. Further still, in various embodiments, the proximal and central portions 42, 45 of the osteotome 40 may be circular in cross-section (i.e., cylindrical) along all or a portion of their lengths, as depicted in the embodiments of the drawings herein, while in other embodiments any of these features may have another type of cross-sectional shape that is other than circular in cross section, for example polyhedral, or may be generally circular or elliptical in cross section.

Referring again to FIG. 5, the osteotome 40 fits into the trajectory guide 10 to contact bone and effect creating a bony corridor. In some embodiments, the trajectory guide 10 includes a cylindrical allograft collection chamber, and the trajectory guide 10 and osteotome 40 fit into standard tubular retractors and are agnostic with respect to receiving standard drill bits or a powered auger insertable through a center through channel 41.

Referring now to FIG. 4 and FIG. 5, the instant disclosure provides a surgical bone cutting system 100 that includes a trajectory guide 10. The trajectory guide 10 includes opposing proximal and distal openings 12, 13 and has a generally cylindrical shape. In some embodiments, the trajectory guide 10 defines a generally hollow bone collection chamber 11 between its proximal and distal openings 12, 13, and the trajectory guide 10 is sized and shaped for insertion within a generally cylindrical surgical retractor 80 that comprises a proximal handle 81 and a distal retractor end 82 for contacting bone, as shown in FIG. 5. In some embodiments, the trajectory guide 10 proximal opening has a shape and dimension that corresponds with the cross-sectional shape and dimension of the distal cutting tip 47 of the osteotome 40.

Referring now to FIGS. 1, 2, 3 and 5, the surgical bone cutting system 100 also includes an osteotome 40 having a generally cylindrical shape and a through channel 41 suitable for receiving a bit 70 inserted therethrough, and a proximal portion 42, a distal portion 43 that includes a cutting jig 44, and a central portion 45 between the proximal portion 42 and the distal portion 43, the cutting jig 44 including a guide shaft 46 and a distal cutting tip 47, the guide shaft 46 being tapered relative to at least the proximal portion 42, and the distal cutting tip 47 having a square or rectangular cross-sectional shape and including opposing pairs of concave radiused cutting edge 48 suitable for penetrating bone. In some embodiments, the guide shaft 46 includes at least one elongate slot aperture 49. In some embodiments, each of the guide shaft 46 and the distal cutting tip 47 has a square cross-sectional shape, and the at least one elongate slot aperture 49 is present in least one of four opposing walls of the guide shaft 50. As depicted in FIGS. 1, 2, 3 and 5, the guide shaft 46 has four walls, one of which includes an elongate slot aperture, and three of which do not have any apertures. It will be appreciated that in various embodiments, whether cylindrical or square in cross-section, the guide shaft 46 may have two or more elongate slot apertures 49 or other openings to facilitate the collection of bone tissue. In the referenced drawings, the guide shaft 46 has a generally square cross-sectional shape that includes four walls, all of which are solid.

In some embodiments, the guide shaft 46 of the osteotome 40 is tapered relative to the central portion 45. In some embodiments, the central portion 45 is generally cylindrical, the central portion 45 including a first pair of opposing sides 51 one or both of the first pair of opposing sides 51 including an elongate aperture that tapers towards the guide shaft 52, the central portion 45 also including a second pair of opposing sides 53 each including concave radiused taper 54. As shown in the drawings, the guide shaft 46 and the distal cutting tip 47 each has a generally square cross-sectional shape.

Figure 6:
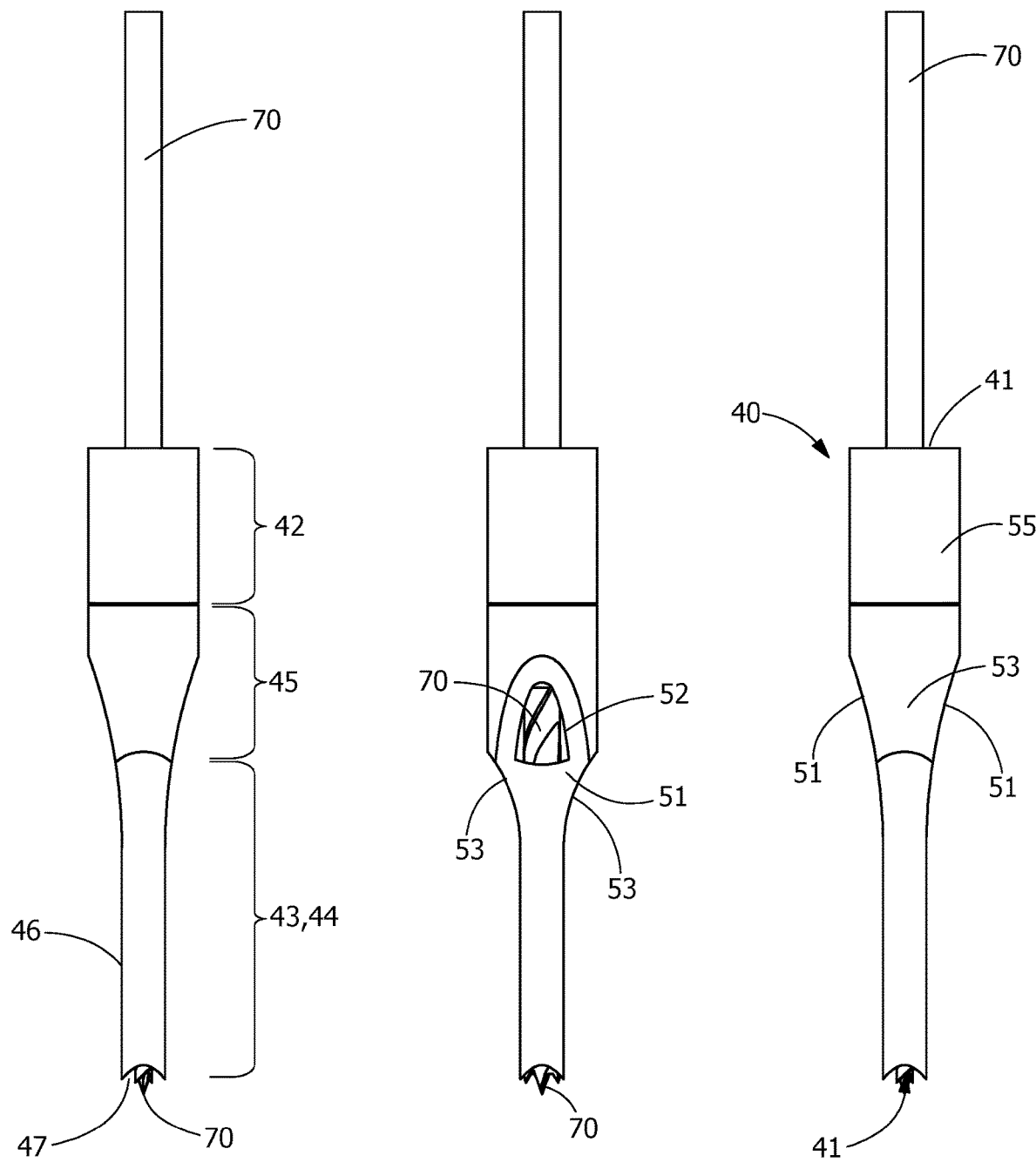
FIG. 6 shows first, second and third side views of a second embodiment of an osteotome of the surgical bone cutting system.
Figure 7:
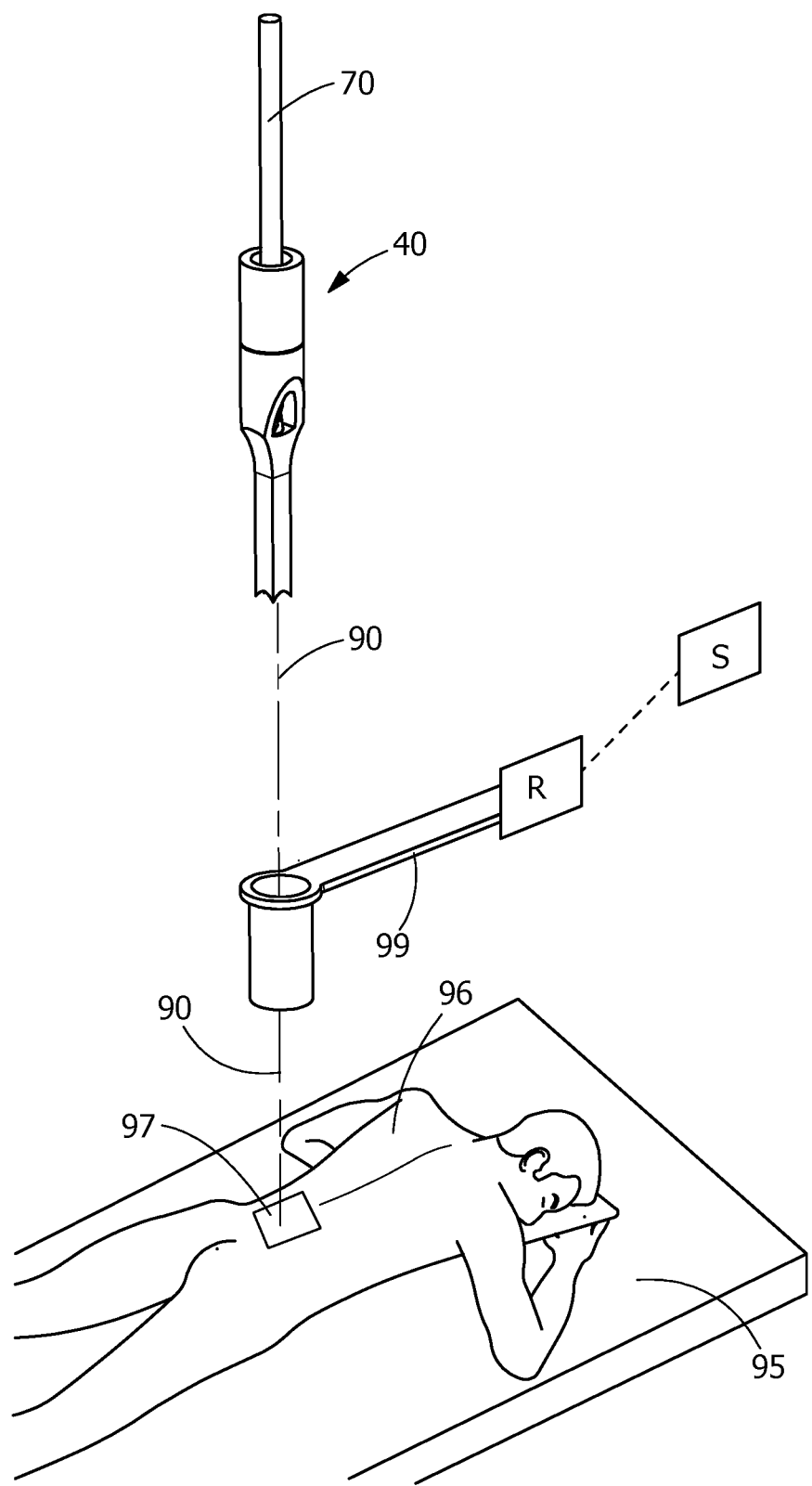
FIG. 7 shows a second embodiment of surgical bone cutting system including the second embodiment of an osteotome as shown in FIG. 6 and a second embodiment of a trajectory guide, all depicted in an exploded view relative to an assembly thereof.

In some embodiments, as shown, for example, in FIGS. 6 and 7, the guide shaft 46 does not have any apertures. In the referenced drawings, the guide shaft 46 may have a generally square cross-sectional shape that includes four walls, all of which are solid. In some embodiments, at least a portion of a solid walled guide shaft 46 may have a cross-sectional shape that is not square, for example, cylindrical or triangular.

Referring again to FIG. 5, the trajectory guide 10 and osteotome 40 are configured to be arranged by passage of at least a portion of the distal portion 43 of the osteotome 40 through the proximal opening of the trajectory guide 10. In some embodiments, the surgical bone cutting system 100 also includes a bone drill or auger comprising a bit 70 suitable for penetrating bone. In some embodiments, as shown variously in the drawings, the proximal portion 42 of the osteotome 40 has a generally cylindrical shape.

According to the first embodiment of the surgical bone cutting system 100 as described above, the surgical bone cutting system 100 is particularly useful for enabling the collection of bone and other biological material that is removed from the surgical site during use of the surgical bone cutting system 100, the collection of the material being accomplished using the embodiment of the trajectory guide 10 as shown in FIG. 4 and FIG. 5, wherein the openings 11, 13 are sized to limit the passage of material from within the hollow bone collection chamber 11. In use, the action of the bit 70 penetrating bone drives excised material upwards whereby it can pass through the at least one elongate slot aperture 49 and collect within the collection chamber 11.

Referring now to FIG. 6 and FIG. 7, the drawings, respectively, show first, second and third side views of a second embodiment of an osteotome 40 of the surgical bone cutting system 100, and a second embodiment of the surgical bone cutting system 100 according to the disclosure, as more fully described herein below, the second embodiment of the surgical bone cutting system 100 including the second embodiment of an osteotome as shown in FIG. 6 and a second embodiment of a trajectory guide, all depicted in an exploded view relative to an assembly thereof.

Referring now to FIG. 7, in some embodiments, the instant disclosure provides a surgical bone cutting system 100 that includes a trajectory guide 10 including opposing proximal and distal openings 12, 13 and an osteotome 40 having a generally cylindrical shape and a through channel 41, and including a proximal portion 42, a distal portion 43 including a cutting jig 44, and a central portion 45 between the proximal portion 42 and the distal portion 43, the cutting jig 44 including a guide shaft 46 and a distal cutting tip 47, the guide shaft 46 being tapered relative to at least the proximal portion 42, and the distal cutting tip 47 having a square or rectangular cross-sectional shape and including opposing pairs of concave radiused cutting edges 48 suitable for penetrating bone.

In some embodiments, the trajectory guide 10 and osteotome 40 are configured to be arranged by passage at least the distal portion 43 of the osteotome 40 through the proximal opening of the trajectory guide 10, the osteotome 40 have a maximum outer diameter that is less than an inner diameter of the trajectory guide 10 to effectively control the trajectory of the inserted osteotome 40 along a trajectory established by the trajectory guide 10 when it is secured to the locking arm 99 and the locking arm 99 is fixed relative to the support substrate 95.

In some embodiments, the surgical bone cutting system 100 also includes a bone drill or auger comprising a bit 70 suitable for drilling bone, and a support substrate 95 for supporting a clinical subject 96, and a locking arm 99 for retaining the trajectory guide 10. Generally, the support substrate 95 is configured to retain a surgical subject 96 in a secured and fixed position, and the locking arm 99 configured to retain the trajectory guide 10 in a secured and fixed position relative to the support substrate 95, the surgical subject 96, or both.

In some embodiments, the locking arm 99 is a robotic arm 99 as shown in FIG. 7, and the surgical bone cutting system 100 further includes an alignment and navigational system that comprises a robot (R) that is controlled by the alignment and navigational system (S) to align the trajectory guide 10 to a target trajectory 90 when connected to the robotic arm 99 within a three dimensional space based on predetermined coordinates, wherein the three dimensional space is defined coordinates that include at least a portion of the support substrate 95, at least a portion of the surgical subject 96, or both.

According to the second embodiment of the surgical bone cutting system 100 as described above, the surgical bone cutting system 100 is particularly useful for enabling precise alignment of the osteotome 40 along a predetermined trajectory (a target trajectory 90) that is established within a coordinate system in three-dimensional space that includes the clinical subject. The trajectory guide 10 is fixed in relation to the clinical subject to precisely orient the through channel of the trajectory guide 10 along the predetermined trajectory and to retain and fix the osteotome 40 along the target trajectory 90 by restricting the motion of the osteotome 40 to movement substantially along the target trajectory 90 (i.e., the outer surface of the osteotome and inner wall of the trajectory guide are tightly toleranced). The surgical bone cutting system 100 thereby ensures that the passage of the osteotome 40 into contact with bone in the surgical site 97 is consistent with a clinically appropriate path and critical biological features in the clinical subject 96 are avoided.

METHODS

Referring now to FIGS. 5 and 7, the disclosure provides a surgical bone cutting system 100 for use according to an inventive method for excising bone from a clinical subject. Referring now to the surgical bone cutting system as depicted in FIG. 5, the disclosure provides a method that includes the step of providing a surgical bone cutting system 100 that includes a trajectory guide 10 including opposing proximal and distal openings 12, 13 and having a generally cylindrical shape and an osteotome 40 having a generally cylindrical shape and a through channel 41 suitable for receiving a bit 70 inserted therethrough, and including a proximal portion 42, a distal portion 43 including a cutting jig 44, and a central portion 45 between the proximal portion 42 and the distal portion 43, the cutting jig 44 including a guide shaft 46 and a distal cutting tip 47, the guide shaft 46 being tapered relative to at least the proximal portion 42, and the distal cutting tip 47 having a square or rectangular cross-sectional shape and including opposing pairs of concave radiused cutting edge 48 suitable for penetrating bone. In some embodiments, the method includes providing a bone drill or auger and a bit 70 suitable for drilling bone.

In some embodiments, the method also includes the steps of establishing access to a surgical site 97 adjacent a bone of a surgical subject 96; positioning and fixing the trajectory guide 10 in a selected position with respect to the surgical site 97; and directing at least a portion of the distal portion 43 of the osteotome 40 through the proximal opening of the trajectory guide 10 and securing the osteotome 40 into engagement with bone in the surgical site 97.

In some embodiments, the access to the surgical site 97 includes securing to the surgical subject 96 one or more instruments selected from the group consisting of a surgical wire, a dilator, a retractor, and a combination thereof.

In some embodiments, the step of establishing access to the surgical site 97 includes securing a cylindrical retractor 80 to the surgical subject 96, and wherein the trajectory guide 10 is sized and shaped for insertion within the cylindrical surgical retractor 80 and defines a generally hollow bone collection chamber 11 between its proximal and distal openings 12, 13.

In some embodiments, the method for excising bone further including the steps of mechanically driving at least a portion of the distal cutting tip 47 into bone followed by passing the bone drill or auger within the through channel 41 of the osteotome 40 and into contact with bone and activating the drill or auger to remove bone tissue.

In some embodiments, the method for excising bone further including collecting bone within the collection chamber 11.

In some embodiments, the instant disclosure provides a method for excising bone from a clinical subject using a predetermined trajectory for access to the surgical site 97, for example, employing coordinates for a target trajectory 90 relative to the surgical site 97 within a three dimensional space, wherein the three dimensional space is defined by coordinates that include at least a portion of the support substrate 95, at least a portion of the surgical subject 96, or both, the method including affixing the trajectory guide 10 to a robotic arm 99, and directing motion of the robotic arm 99 to position the trajectory guide 10 into alignment with the target trajectory 90.

In some embodiments, the osteotome 40 has a maximum outer diameter that is less than an inner diameter of the trajectory guide 10. In some embodiments, the surgical bone cutting system 100 further includes a support substrate 95; and a locking arm 99, the support substrate 95 configured to retain the surgical subject 96 in a secured and fixed position, the locking arm 99 configured to retain the trajectory guide 10 in a secured and fixed position relative to the support substrate 95, the surgical subject 96, or both.

In some embodiments, the method for excising bone further includes, after the step of establishing access to the surgical site 97, securing the trajectory guide 10 to the locking arm 99 and fixing the locking arm 99 relative to the support substrate 95; and passing at least the distal portion 43 of the osteotome 40 through the proximal opening of the trajectory guide 10 whereby interference between an outer wall of the osteotome 55 and an inner wall of the trajectory guide 15 effectively controls the trajectory of the inserted osteotome 40 along a trajectory established by the trajectory guide 10.

In some embodiments, the locking arm 99 is a robotic arm 99, the surgical bone cutting system 100 further including an alignment and navigational system that comprises a robot (R) that is controlled by the navigational system.

In some embodiments, the method for excising bone further includes providing coordinates for a target trajectory 90 relative to the surgical site 97 within a three dimensional space, wherein the three dimensional space is defined by coordinates that include at least a portion of the support substrate 95, at least a portion of the surgical subject 96, or both, affixing the trajectory guide 10 to the robotic arm 99, and directing motion of the robotic arm 99 to position the trajectory guide 10 into alignment with the target trajectory 90.

In some embodiments, the step of establishing access to the surgical site 97 includes selecting a surgical site 97 within a human spine and wherein the selected surgical site 97 is adjacent bone that is a facet joint, the method for excising bone further including one or more of the steps of mechanically driving at least a portion of the distal cutting tip 47 of the osteotome 40 into bone followed by removing the osteotome 40 from the trajectory guide 10, and mechanically driving at least a portion of the distal cutting tip 47 into bone followed by passing the bone drill or auger within the through channel 41 of the osteotome 40 and into contact with bone and activating the drill or auger to remove bone tissue. In some particular embodiments, the method includes specifically mechanically driving at least a portion of the distal cutting tip 47 of the osteotome 40 into bone followed by removing the osteotome 40 from the trajectory guide 10, followed by insertion of one or more other surgical instruments into the surgical site 97 to manipulate bone or soft tissue therein.

Any one of the steps according to the embodiments of the inventive methods as described herein may be repeated, including the steps of introducing and removing the osteotome 40 from the surgical site 97, in any order or combination, to effect bone penetration and/or removal.

While various inventive aspects, concepts, and features of the general inventive concepts are described and illustrated herein in the context of various exemplary embodiments, these various aspects, concepts, and features may be used in many alternative embodiments, either individually or in various combinations and sub-combinations thereof. Unless expressly excluded herein, all such combinations and sub-combinations are intended to be within the scope of the general inventive concepts. Still further, while various alternative embodiments as to the various aspects, concepts, and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts, or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary, or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention.

Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

What is claimed is:

1. A surgical bone cutting system, comprising:
   i. a trajectory guide comprising opposing proximal and distal openings and having a generally cylindrical shape;
   ii. an osteotome having a through channel suitable for receiving a bit suitable for penetrating bone inserted therethrough, and comprising a proximal portion, a distal portion comprising a cutting jig, and a central portion between the proximal portion and the distal portion, the cutting jig comprising a guide shaft and a distal cutting tip, the guide shaft being tapered relative to at least the proximal portion, and the distal cutting tip having a square or rectangular cross-sectional shape and comprising opposing pairs of concave radiused cutting edges suitable for penetrating bone; and
   iii. a bone drill or auger comprising a bit suitable for penetrating bone,
   wherein the trajectory guide and osteotome are configured to be arranged by passage of at least a portion of the distal portion of the osteotome through the proximal opening of the trajectory guide.

2. The surgical bone cutting system according to claim 1, wherein the proximal portion of the osteotome has a generally cylindrical shape.

3. The surgical bone cutting system according to claim 1, wherein the trajectory guide defines a generally hollow bone collection chamber between its proximal and distal openings, and wherein the trajectory guide is sized and shaped for insertion within a generally cylindrical surgical retractor that comprises a proximal handle and a distal retractor end for contacting bone.

4. The surgical bone cutting system according to claim 1, the guide shaft comprising at least one elongate slot aperture.

5. The surgical bone cutting system according to claim 4, wherein each of the guide shaft and the distal cutting tip has a square cross-sectional shape, and the at least one elongate slot aperture is present in least one of four opposing walls of the guide shaft.

6. The surgical bone cutting system according to claim 1, wherein the trajectory guide proximal opening has a shape and dimension that corresponds with the cross-sectional shape and dimension of the distal cutting tip of the osteotome.

7. The surgical bone cutting system according to claim 1, wherein the guide shaft of the osteotome is tapered relative to the central portion.

8. The surgical bone cutting system according to claim 1, wherein the central portion is generally cylindrical, the central portion comprising a first pair of opposing sides, one or both of the first pair of opposing sides comprising an elongate aperture that tapers towards the guide shaft, the central portion also comprising a second pair of opposing sides each comprising concave radiused taper.

9. A surgical bone cutting system, comprising:
   i. a trajectory guide comprising opposing proximal and distal openings;
   ii. an osteotome having a through channel, and comprising a proximal portion, a distal portion comprising a cutting jig, and a central portion between the proximal portion and the distal portion, the cutting jig comprising a guide shaft and a distal cutting tip, the guide shaft being tapered relative to at least the proximal portion, and the distal cutting tip having a square or rectangular cross-sectional shape and comprising opposing pairs of concave radiused cutting edges suitable for penetrating bone;
   iii. a bone drill or auger comprising a bit suitable for penetrating bone, and
   iv. a support substrate and a locking arm, the support substrate configured to retain a surgical subject in a secured and fixed position, the locking arm configured to retain the trajectory guide in a secured and fixed position relative to the support substrate, the surgical subject, or both,
   wherein the trajectory guide and osteotome are configured to be arranged by passage at least the distal portion of the osteotome through the proximal opening of the trajectory guide, the osteotome have a maximum outer diameter that is less than an inner diameter of the trajectory guide to effectively control the trajectory of the inserted osteotome along a trajectory established by the trajectory guide when it is secured to the locking arm and the locking arm is fixed relative to the support substrate.

10. The surgical bone cutting system according to claim 1, wherein the locking arm is a robotic arm, the surgical bone cutting system further comprising an alignment and navigational system that comprises a robot that is controlled by the navigational system to align the trajectory guide when connected to the robotic arm within a three dimensional space based on predetermined coordinates, wherein the three dimensional space is defined coordinates that include at least a portion of the support substrate, at least a portion of the surgical subject, or both.

11. A method for excising bone from a clinical subject, the method comprising:
   a. providing a surgical bone cutting system that includes
      i. a trajectory guide comprising opposing proximal and distal openings and having a generally cylindrical shape;
      ii. an osteotome having a through channel suitable for receiving a bit suitable for penetrating bone inserted therethrough, and comprising a proximal portion, a distal portion comprising a cutting jig, and a central portion between the proximal portion and the distal portion, the cutting jig comprising a guide shaft and a distal cutting tip, the guide shaft being tapered relative to at least the proximal portion, and the distal cutting tip having a square or rectangular cross-sectional shape and comprising opposing pairs of concave radiused cutting edges suitable for penetrating bone; and
      iii. a bone drill or auger and a bit suitable for penetrating bone
   b. establishing access to a surgical site adjacent a bone of a surgical subject;
   c. positioning and fixing the trajectory guide in a selected position with respect to the surgical site;
   d. directing at least a portion of the distal portion of the osteotome through the proximal opening of the trajectory guide and securing the osteotome into engagement with bone in the surgical site.

12. The method for excising bone according to claim 11, wherein the access to the surgical site includes securing to the surgical subject one or more instruments selected from the group consisting of a surgical wire, a dilator, a retractor, and a combination thereof.

13. The method for excising bone according to claim 12, wherein the step of establishing access to the surgical site includes securing a cylindrical retractor to the surgical subject, and wherein the trajectory guide is sized and shaped for insertion within the cylindrical surgical retractor and defines a generally hollow bone collection chamber between its proximal and distal openings.

14. The method for excising bone according to claim 13, the method for excising bone further comprising the steps of mechanically driving at least a portion of the distal cutting tip into bone followed by passing the bone drill or auger within the through channel of the osteotome and into contact with bone and activating the drill or auger to remove bone tissue.

15. The method for excising bone according to claim 14, the method for excising bone further comprising collecting bone within the collection chamber.

16. The method for excising bone according to claim 11, wherein the osteotome has a maximum outer diameter that is less than an inner diameter of the trajectory guide, the surgical bone cutting system further comprising;
    iv. a support substrate; and
    v. a locking arm, the support substrate configured to retain the surgical subject in a secured and fixed position, the locking arm configured to retain the trajectory guide in a secured and fixed position relative to the support substrate, the surgical subject, or both.

17. The method for excising bone according to claim 16, the method for excising bone further comprising, after the step of (c) establishing access to the surgical site, the steps comprising:
    securing the trajectory guide to the locking arm and fixing the locking arm relative to the support substrate; and
    passing at least the distal portion of the osteotome through the proximal opening of the trajectory guide whereby interference between an outer wall of the osteotome and an inner wall of the trajectory guide effectively controls the trajectory of the inserted osteotome along a trajectory established by the trajectory guide.

18. The method for excising bone according to claim 17, wherein the locking arm is a robotic arm, the surgical bone cutting system further comprising
    vi. an alignment and navigational system that comprises a robot that is controlled by the navigational system.

19. The method for excising bone according to claim 18, the method for excising bone further comprising, providing coordinates for a target trajectory relative to the surgical site within a three dimensional space, wherein the three dimensional space is defined by coordinates that include at least a portion of the support substrate, at least a portion of the surgical subject, or both, affixing the trajectory guide to the robotic arm, and directing motion of the robotic arm to position the trajectory guide into alignment with the target trajectory.

20. The method for excising bone according to claim 19, wherein the step of establishing access to the surgical site includes selecting a surgical site within a human spine and wherein the selected surgical site is adjacent bone that is a facet joint, the method for excising bone further comprising the step selected from the group consisting of (1) mechanically driving at least a portion of the distal cutting tip into bone followed by removing the osteotome from the trajectory guide, (2) mechanically driving at least a portion of the distal cutting tip into bone followed by passing the bone drill or auger within the through channel of the osteotome and into contact with bone and activating the drill or auger to remove bone tissue, and (3) a combination thereof.

* * * * *